United States Patent
Squyres

[19]

[11] Patent Number: 5,201,576
[45] Date of Patent: Apr. 13, 1993

[54] SHADOWLESS SPHERICAL ILLUMINATION SYSTEM FOR USE IN AN ARTICLE INSPECTION SYSTEM

[75] Inventor: Henry P. Squyres, Medford, Oreg.

[73] Assignee: Simco/Ramic Corporation, Medford, Oreg.

[21] Appl. No.: 876,922

[22] Filed: Apr. 30, 1992

[51] Int. Cl.$^5$ ............................................. G03B 15/00
[52] U.S. Cl. ........................................ 362/3; 362/216; 362/253; 362/347; 356/394
[58] Field of Search ............... 362/16, 5, 8, 216, 234, 362/253, 347, 350, 3; 356/236, 394; 250/228

[56] References Cited

U.S. PATENT DOCUMENTS

| | | | |
|---|---|---|---|
| 4,500,203 | 2/1985 | Bieringer | 356/394 |
| 4,651,262 | 3/1987 | Piironen | 362/350 |
| 4,988,202 | 1/1991 | Nayar et al. | 356/394 |

FOREIGN PATENT DOCUMENTS 2159617 11/1985 United Kingdom ............... 362/216

Primary Examiner—Ira S. Lazarus
Assistant Examiner—L. Heyman
Attorney, Agent, or Firm—Stoel Rives Boley Jones & Grey

[57] ABSTRACT

A shadowless illumination system (10) according to the present invention includes a spherical chamber (14) having a chamber entrance opening (18) and a chamber exit opening (20). The inside surface (32) of the spherical chamber is coated with highly reflective flat white paint. A clear rigid plastic cylindrical tube (22) is positioned in the spherical chamber between the chamber entrance and exit openings. A circular fluorescent ring lamp (36) is positioned inside the spherical chamber to form an annulus around the tube. The lamp and the white inside surface of the spherical chamber provide shadowless illumination for articles (30) that are dropped or otherwise projected through the tube. The articles are inspected as they pass through the tube by at least two video inspection cameras (52 and 62) that view opposite sides of the articles through respective viewing openings (44 and 48). Whenever no articles are present in the image plane of a camera, the lamp provides a saturated background for the camera. A ballast (140) controls the voltage to the lamp to provide constant light intensity.

20 Claims, 3 Drawing Sheets

5,201,576

SHADOWLESS SPHERICAL ILLUMINATION SYSTEM FOR USE IN AN ARTICLE INSPECTION SYSTEM

TECHNICAL FIELD

The present invention relates to a shadowless spherical illumination system for use in an article inspection system.

BACKGROUND OF THE INVENTION

Optical defect inspection systems have been used to identify defects in articles such as fruits and vegetables, processed meats, baked goods, and nonfood items. These inspection systems typically employ laser-based scanning or charge-coupled device-based video cameras to detect undesirable variations in the shade of the article passing through a scanning area. In some inspection systems, inspection equipment create shadows which may be mistaken for defects or otherwise make identification of defects unreliable.

Shadowless performance has been obtained by using many, for example, twenty-six, incandescent lamps in a generally spherical arrangement around the articles being inspected. The lamps are used in connection with reflectors, iris apertures, and projection lenses. Shadowless illumination of the articles positioned at an image plane requires adjustment and alignment of the lamps with the apertures until cameras view even illumination from all sides of a white test target. In addition to the twenty-six incandescent lamps, the system uses two fluorescent lamps that provided a saturated background having a brightness over 10% above the brightness of a white test object in the image plane.

The incandescent lamps of the prior system are operated at a regulated voltage that is much lower than their normal operating voltage in order to maintain a relatively stable light output and stable spectral distribution over a reasonable period of time. Despite the low operating voltage, the twenty-six lamp system requires 540 watts to produce a light level of 500 footlamberts over a seven inch (178 millimeter) wide image plane. However, the lamps become uncalibrated with time because of lamp aging. There has been no way to keep the light output on the article calibrated other than the regulation of the DC power supply that powers the lamps. Because of the above-mentioned characteristics, these prior systems have been expensive to build and operate and difficult to maintain.

SUMMARY OF THE INVENTION

It is, therefore, an object of the present invention to provide shadowless performance in an illumination system that is relatively inexpensive to build and operate, and easy to maintain.

Another object of the invention is to provide an illumination system that provides constant light output without recalibration despite lamp aging.

A shadowless illumination system according to the present invention includes a spherical chamber having a chamber entrance opening and a chamber exit opening. The inside surface of the spherical chamber is coated with highly reflective flat white paint. A clear rigid plastic cylindrical tube is positioned in the spherical chamber between the chamber entrance and exit openings. A circular fluorescent ring lamp is positioned inside the spherical chamber to form an annulus around the tube. The lamp and the white inside surface of the spherical chamber provide shadowless illumination for articles that are dropped or otherwise projected through the tube. The articles are inspected as they pass through the tube by at least two video cameras that view opposite sides of the articles through respective viewing openings. Whenever no articles are present in the image plane of a video camera, the lamp provides a saturated background for the video camera. A ballast controls the voltage to the lamp to provide constant light intensity.

Additional objects and advantages of the present invention will be apparent from the following detailed description of a preferred embodiment thereof, which proceeds with reference to the accompanying drawings.

DETAILED DESCRIPTION OF PREFERRED EMBODIMENTS

Figure 1:
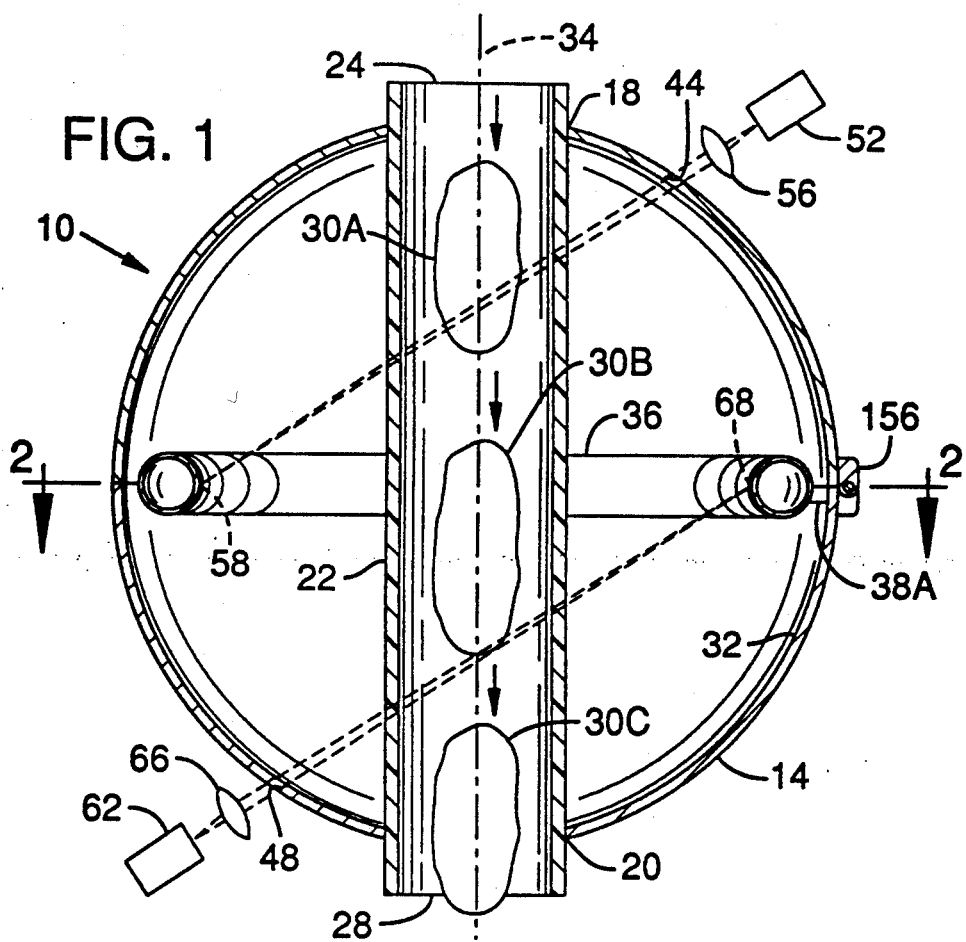
FIG. 1 shows a cross-sectional side view of a two camera shadowless spherical illumination system according to the present invention.
Figure 2:
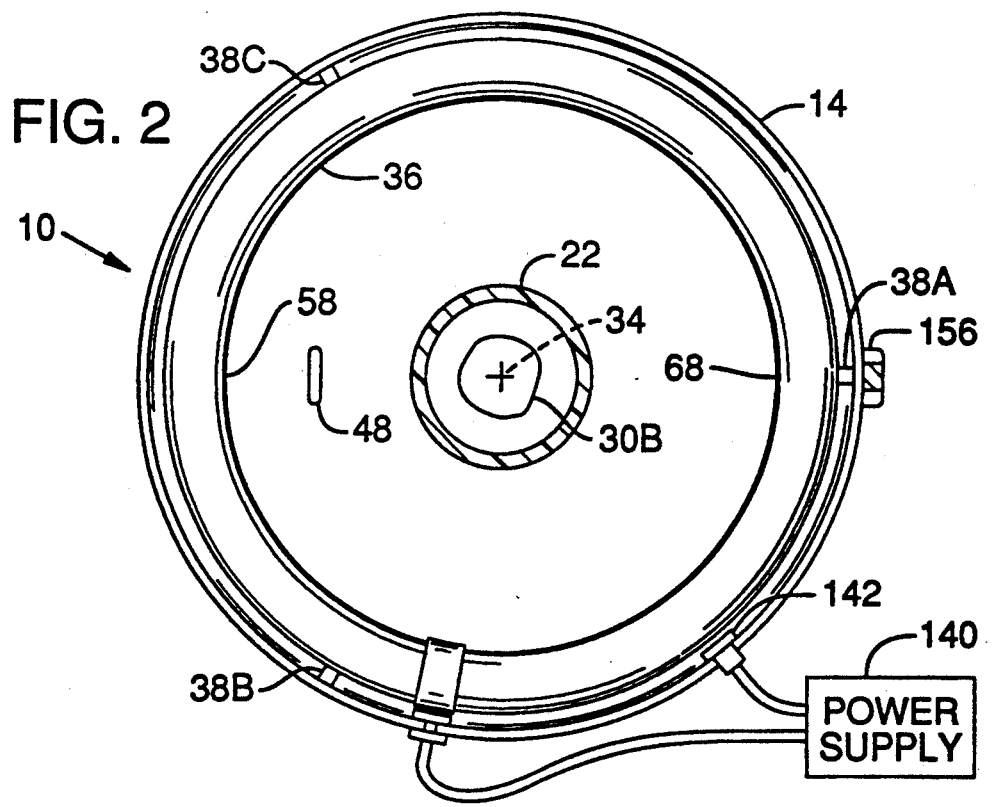
FIG. 2 shows a plan view of the lower interior portion of the system of FIG. 1.

Referring to FIGS. 1 and 2, a shadowless spherical illumination system 10 includes an integrating spherical chamber 14 with a chamber entrance opening 18 and a chamber exit opening 20 positioned at opposite poles of spherical chamber 14. FIG. 2 shows a plan view of system 10 taken along lines 2—2 of FIG. 1. A clear rigid plastic (e.g., Plexiglass ®) cylindrical tube 22 extends between entrance opening 18 and exit opening 20. Tube 22 includes a tube entrance opening 24 and a tube exit opening 28.

In operation, articles 30 to be inspected, such as potatoes 30A, 30B, and 30C, are passed through tube 22 from tube entrance opening 24 to tube exit opening 28. The invention is not restricted to longitudinal axis 34 of tube 22 having a particular relationship to the direction of the force of gravity. However, in order to keep the surface of tube 22 clean, it is desirable to minimize contact between articles 30 and tube 22. Therefore, in a preferred embodiment, the relationship between longitudinal axis 34 of tube 22 and the direction of the force of gravity depends on the horizontal velocity of articles 30 passing through tube entrance opening 24. For example, if articles 30 have zero horizontal velocity, then it is preferred that longitudinal axis 34 be parallel to the direction of the force of gravity. If articles have a nonzero horizontal velocity, then it is preferred that longitudinal axis 34 be at an angle to the force of gravity to minimize contact between articles 30 and the interior surface of tube 22.

Inside surface 32 of spherical chamber 14 is coated with flat white paint providing reflectivity above 90%. The flat white paint may be an acrylic flat white paint

7790, manufactured by Krylon, of Vernon Hills, Ill. The flat white paint is preferred because it performs adequately and is far less expensive than titanium oxide, which is used in some high-performance optical integrating spheres.

A circular fluorescent ring lamp 36 is positioned inside spherical chamber 14 to form an annulus around tube 22. Lamp 36 and reflecting inside surface 32 create an effective spherical shadowless light source that substantially reduces the spurious video features that can be caused by shadows formed by unidirectional light sources and specular glare from foreign substances such as water. Articles 30 are illuminated over virtually their entire surface with spherical regulated uniform illumination that virtually does not change optical spectral distribution at any point in the image plane with time. Whenever no articles 30 are present in the image plane of a video camera, lamp 36 provides a saturated background for the video camera.

Lamp 36 is preferably positioned half-way between chamber entrance opening 18 and exit opening 20 (i.e., at the equator of spherical chamber 14.) Lamp 36 defines a plane which is preferably perpendicular to longitudinal axis 34 of tube 22. Lamp 36 is attached to the inside of spherical chamber 14 by means of three brackets 38A, 38B, and 38C (shown in FIG. 2) spaced 120° around the equator of spherical chamber 14.

Articles 30 may be inspected by two or more cameras. FIG. 1 shows a two camera system. Referring to FIG. 1, spherical chamber 14 includes an upper viewing opening 44 and a lower viewing opening 48. A camera 52 is positioned so its axis is directed through a lens 56 and upper viewing opening 44 toward a point 58 on lamp 36. A camera 62 is positioned so its axis is directed through a lens 66 and lower viewing opening 48 to a point 68 on lamp 36. Points 58 and 68 are 180° apart with respect to the axis at the center of lamp 36 (which coincides with longitudinal axis 34 of tube 22). Therefore, cameras 52 and 62 view both sides of articles 30. Lamp 36 acts as a saturated background for cameras 52 and 62 that helps the cameras shutter against articles 30 moving through the respective image planes of the cameras. The background illumination level is preferably at least 10% higher than a white lambertian reflective object in the image plane of the camera.

Figure 3:
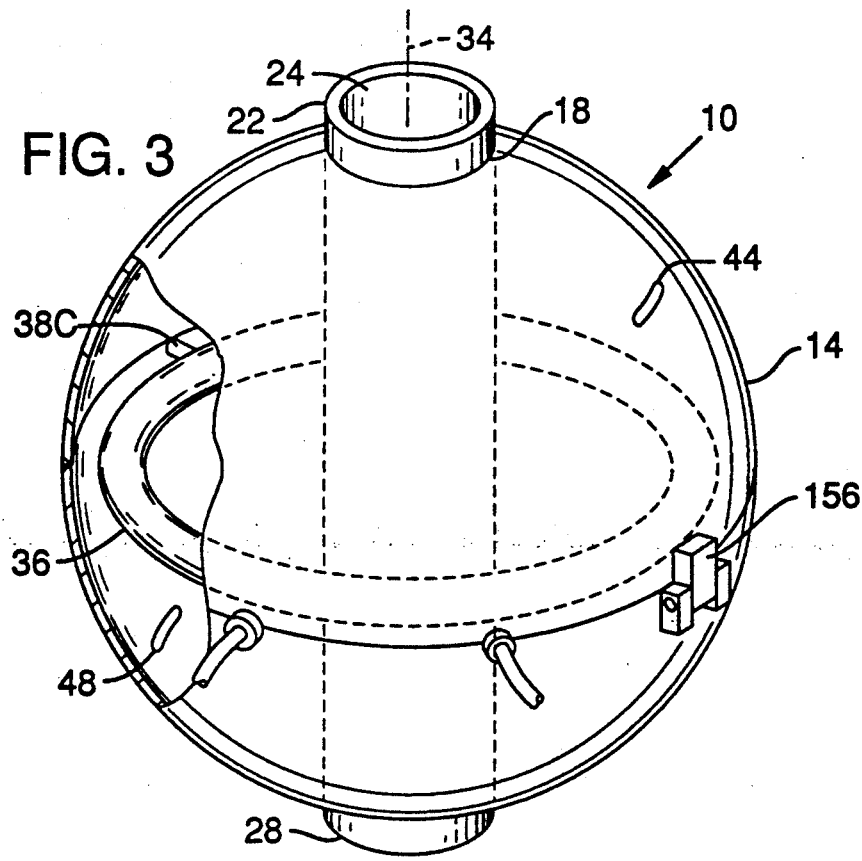
FIG. 3 shows an elevated side view partly cut away of the system of FIG. 1 rotated by about 15°.

Viewing openings 44 and 48 may be shaped as slits, as shown in FIG. 3, which are sized to function as field stops that restrict the field of view of cameras 52 and 62. In a preferred embodiment in which the diameter of the equator of spherical chamber 14 is twenty-eight inches (711 millimeters), viewing openings 44 and 48 each have dimensions of ⅛th inch (3.2 millimeters) by two inches (50.8 millimeters). Viewing openings 44 and 48 may be, but are preferably not, covered by a transparent material.

Cameras 52 and 62 are preferably CCD (charge coupled device) line scan cameras. Those skilled in the art will appreciate that cameras 52 and 62 may be any of a variety of types of cameras marketed by a variety of vendors, such as model CCD1300 marketed by Fairchild. A preferable line scan camera is described in pending U.S. patent application No. 07/606,758 filed Oct. 30, 1990, entitled "Color Line Scan Video Camera for Inspection System," invented by Heffington et al, and assigned to the assignee of the present application. In a preferred embodiment, cameras 52 and 62 each comprise one row of 1,024 pixels, in which each pixel is about 14 microns by 14 microns. The field of view of cameras 52 and 62 is provided by lenses 56 and 66, and should cover the width of tube 22. Therefore, in the case in which tube 22 is seven inches (178 millimeters) wide, the fields of view of cameras 52 and 62 are also seven inches (178 millimeters).

In two camera inspection systems, each camera views one-half of articles 30. There can be some inaccuracy in determining whether defects exist at the edges of an article 30 viewed by each camera. The problem may be overcome by using more than two cameras so the areas viewed by the cameras overlap. The information from each camera is stored in digital memory. The information from the edges of the viewing area of each camera are ignored in determining defects. In addition, the remainder of the overlapping portion may be divided so that information from only one camera is considered or, alternatively, information from more than one camera may be considered. The information from the cameras may be processed by standard well known techniques.

Figure 4:
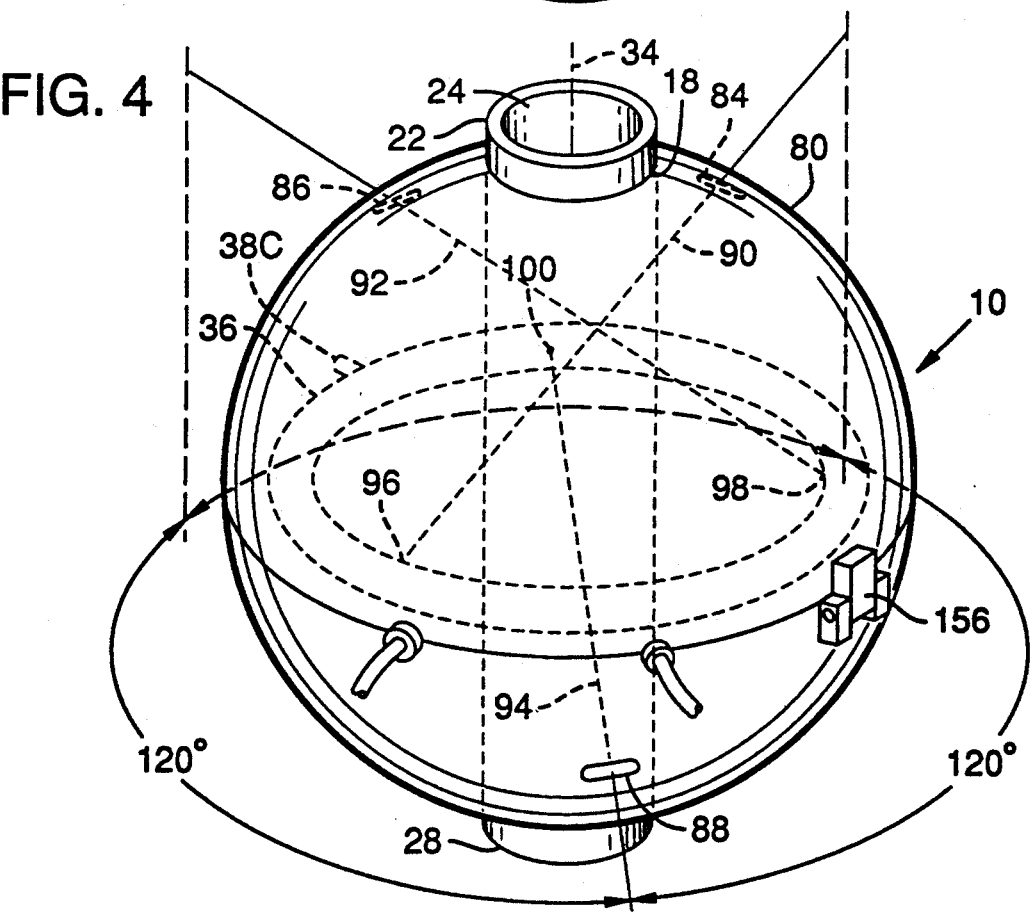
FIG. 4 shows a side elevation view of a three camera shadowless spherical illumination system according to the present invention.

FIG. 4 shows system 10 with spherical chamber 80, which is used with three cameras. Spherical chamber 80 is identical to spherical chamber 14, except that spherical chamber 80 has three viewing openings 84, 86, and 88 rather than two viewing openings. Viewing openings 84, 86, and 88 are preferably positioned so that axes 90, 92, and 94 of three cameras (not shown) extend through ones of viewing openings 84, 86, and 88 toward points 96, 98, and 100, respectively, on lamp 36. Points 96, 98, and 100 are spaced 120° apart with respect to the center of lamp 36 (which is on axis 34).

Figure 5:
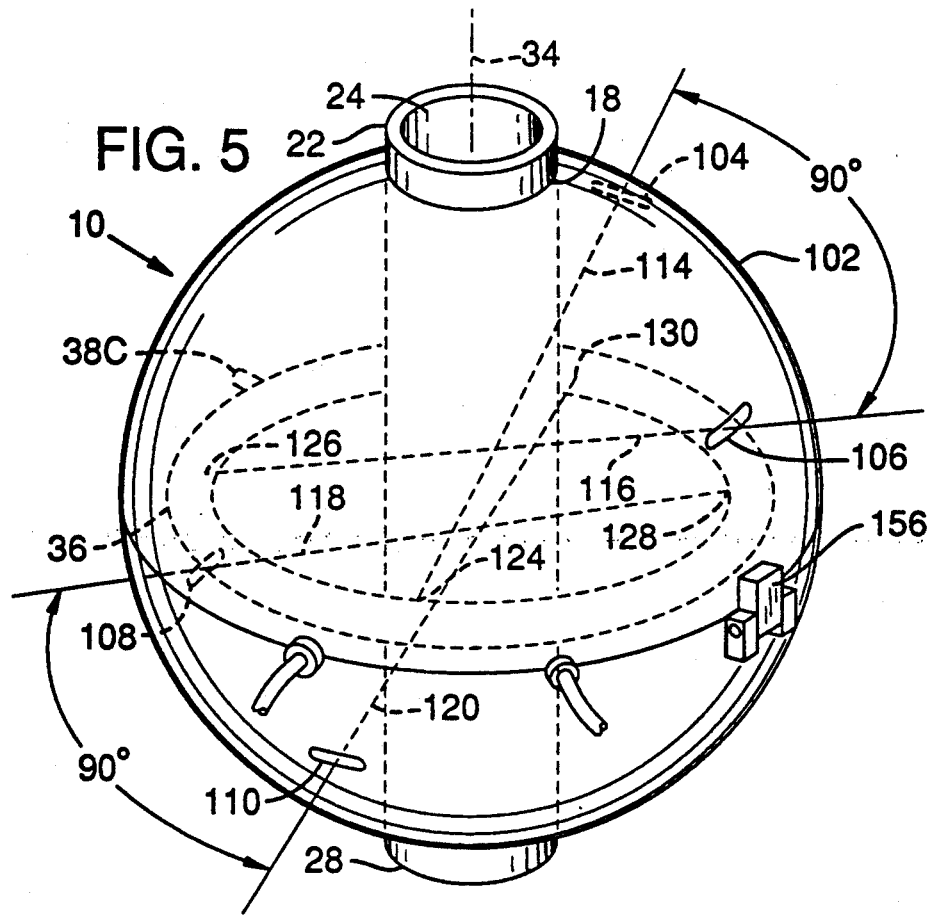
FIG. 5 shows a side view of a four camera shadowless spherical illumination system according to the present invention.

FIG. 5 shows system 10 with spherical chamber 102, which is used with four cameras. Spherical chamber 102 is identical to spherical chamber 14, except that spherical chamber 102 has four viewing openings 104, 106, 108, and 110 rather than two viewing openings. Viewing openings 104, 106, 108, and 110 are preferably positioned so that axes 114, 116, 118, and 120 of four cameras (not shown) extend through ones of viewing openings 104, 106, 108, and 110 toward points 124, 126, 128, and 130, respectively, on lamp 36. Points 124, 126, 128, and 130 are spaced 90° apart with respect to the center of lamp 36 (which is on axis 34).

Factors influencing the number of cameras used include the expense of additional cameras and the accuracy required in determining the amount and kinds of defects.

The invention is not restricted to a particular diameter for lamp 36. It is believed that the best performance would occur where lamp 36 has a diameter that is only slightly smaller than that of spherical chamber 14, such as is shown in FIGS. 1 and 2. However, the largest commercially available ring lamp the inventor could locate has a diameter of sixteen inches (406.4 millimeters), and is marketed under the name Sylvania FC16T9RS by GTE of Danvers, Mass. It is believed that the sixteen inch (406.4 millimeter) diameter lamp 36 in a twenty-eight inch (711 millimeter) diameter spherical chamber 14 and a seven inch (178 millimeter) diameter tube 22 provides adequate performance for most applications. Lamp 36 preferably produces light levels above 500 footlamberts for silicon type CCD cameras to operate at frame rates of 500 microseconds per frame. It is believed that light output of 1,000 footlamberts on articles 30 is acceptable for many applications.

In a preferred embodiment, the diameter of the equator of spherical chamber 14 is twenty-eight inches (711 millimeters), and the diameter of tube 22 is seven inches (178 millimeters). There are tradeoffs in the performance of spherical chambers 14, 80, and 102 as the dimensions of various components changes. First, there is a decrease in total reflectivity with an increase in the size of openings 18 and 20 in spherical chamber 14. The accuracy of inspection in spherical chamber 14 may be reduced by a decrease in reflectivity. Second, if the diameter of tube 22 is too small, articles 30 passing through tube 22 will be more likely to touch the surface of tube 22. It is believed that a ratio of the diameter of tube 22 to the diameter of the equator of spherical chamber 14 equal to one-quarter is acceptable for many applications. It is believed that light uniformity within tube 22 is acceptable for many applications when the area of openings 18 and 20 and viewing openings amounts to less than about 10% of the total surface area of the spherical chamber. Depending on the application, light uniformity may be acceptable with a larger percentage used for openings 18 and 20 and viewing openings.

The following are tradeoffs in increasing the diameter of spherical chamber 14. An increase in the diameter of spherical chamber 14 would allow an increase in the diameter of openings 18 and 20 and tube 22 while maintaining at least a one-quarter ratio between the diameter of tube 22 and spherical chamber 14. Also, if the diameter of openings 18 and 20 and tube 22 is seven inches (178 millimeters), an increase in the diameter of spherical chamber 14 would lead to a decrease in the percentage of total spherical chamber surface area cut away for openings, thus leading to an increase in illumination performance. However, as noted above, if the diameter of lamp 36 is not increased, there might be a decrease in illumination performance. Illumination performance could be maintained or increased by using a lamp 36 with a larger diameter. However, the cost of doing so may be very expensive unless a lamp 36 with a diameter greater than sixteen inches (406.4 millimeters) is commercially available. Finally, the cost of constructing spherical chamber 14 increases with an increase in the diameter of spherical chamber 14.

Lamp 36 is maintained at a predetermined constant intensity by an electronic ballast 140, shown in FIG. 2. Ballast 140 may be of the type marketed under part number FL096-4 by Mercron of Richardson, Tex. Ballast 140 operates at a frequency of 40 KHz to 50 KHz, which is much higher than the scan rate of the cameras so as to avoid flicker. A photosensor 142 detects variations in the intensity of the light source. In response to these variations, the ballast varies the frequency at which lamp 36 operates, thereby to maintain the constant intensity. Ballast 140 includes an inductor (not shown) in series with lamp 36, which has low impedance. The reactance of the circuit comprising the inductor and lamp 36 is controlled by varying the frequency of ballast 140. Consequently, the voltage applied to lamp 36 is also controlled by varying the frequency of ballast 140. Because only one lamp 36 is used to illuminate spherical chamber 14 and provide a background for cameras 52 and 62, and feedback is provided by ballast 140, the light output of the system 10 remains constant despite aging of lamp 36.

The present invention may be used in either a defect removal or a statistical inspection system. A defect removal inspection systems detects defects in articles and removes the defects from the articles or removes the article from the inspection line so the article is not used. An statistical inspection system keeps track of the amount, and perhaps also type, of defects in articles, but does not necessarily remove defects. The present invention is particularly well suited for an inexpensive statistical inspection system. For example, a certain group of potatoes may have a grade that is acceptable for stew, but not for french fries. A statistical inspection system allows a food processor to precisely match a customer's food quality standards without incurring the costs (e.g., through high reject rates) of surpassing those standards.

Figure 6:
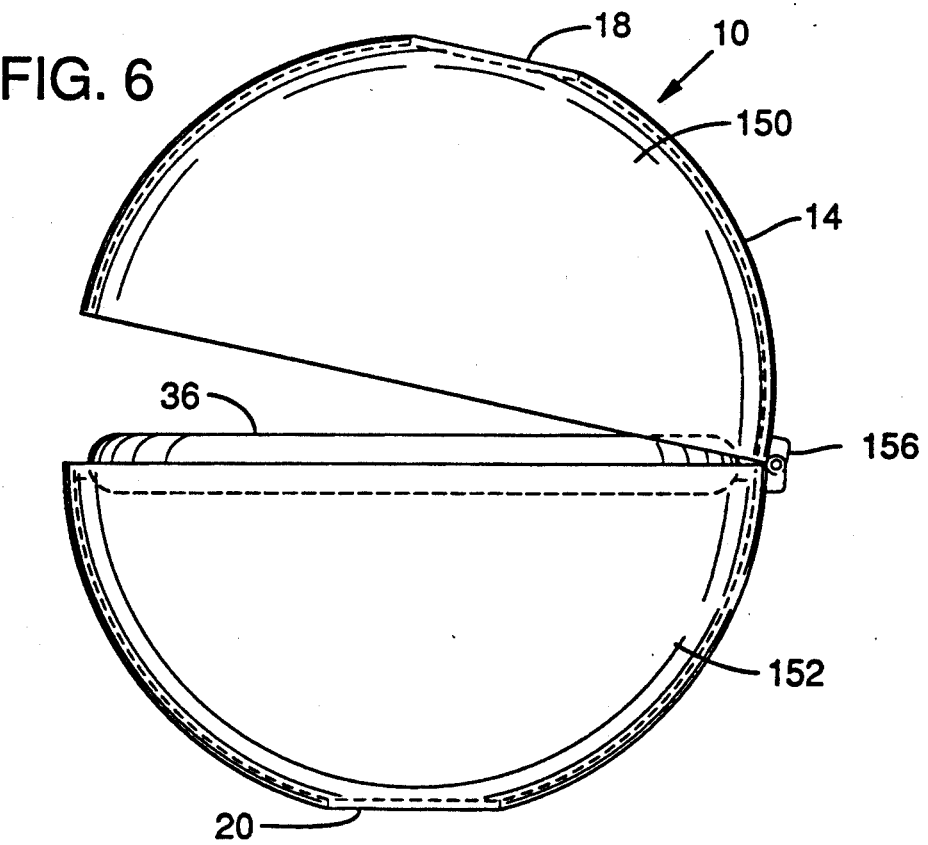
FIG. 6 shows hemispheres of the system of FIG. 1 joined by a hinge.

Referring to FIG. 6, spherical chamber 14 is preferably formed by hemispheres 150 and 152. When food articles are inspected, it is expected that water and other debris such as starch carried on the articles will be deposited on tube 22. In that case, the water and debris may prevent cameras 52 and 62 from accurately detecting defects on the articles. Accordingly, it is desirable to regularly clean tube 22. The time during which system 10 is inoperative may be minimized by replacing a dirty tube 22 with a clean tube 22 and immediately restarting operation of illumination system 10, rather than waiting until the dirty tube 22 is cleaned. To replace tube 22 and lamp 36, spherical chamber 14 may be opened by separating hemispheres 150 and 152, which may be hinged together by hinge 156. Spherical chamber 14 is preferably constructed of aluminum. Preferably, each hemisphere of spherical chamber 14 is formed by spinning a sheet of (e.g., ⅛th inch (3.2 millimeter) thick) aluminum while pressing it against a solid hardwood jig.

Integrating spheres have been used in optics laboratories as a source of flat (i.e., shadowless) white light. However, these integrating spheres differ from the invention in several ways. For example, articles are not passed through these integrating spheres for inspection. In addition, the integrating spheres are typically formed to very high tolerances, include multiple incandescent light sources positioned within the sphere, and have very expensive titanium oxide coatings to form the white surfaces.

Those having skill in the art will appreciate that many changes may be made in the above-identified details of a preferred embodiment of the present invention without departing from the underlying principles thereof. For example, although it is preferably circular, the cross section of tube 22 may be a nonround shape such as a square. System 10 may employ circular or noncircular lamps in addition to lamp 36, and may use one or more noncircular lamps instead of lamp 36. The axes of the cameras are preferably positioned to view points that are evenly spaced around lamp 36. However, the cameras do not have to be positioned to view evenly spaced points, and do not have to be positioned to view points on lamp 36. The scope of the present invention should, therefore, be determined only by the following claims.

I claim:

1. A shadowless illumination system, comprising:
   a spherical chamber having a reflective inside surface, and chamber entrance and exit openings;
   a transparent tube positioned inside the chamber between the chamber entrance opening and the chamber exit opening;
   a light source providing illumination inside the chamber; and
   the chamber including a number of viewing openings positioned such that a corresponding number of inspection cameras may be positioned to view all portions of an article passing through the tube.

2. The system of claim 1 in which the light source is a ring lamp positioned inside the chamber and around the tube.

3. The system of claim 2 in which the ring lamp has a center and each of the cameras has an optical axis, and in which each of the viewing openings is positioned such that the cameras may be positioned so their respective axes are directed to corresponding points on the ring lamp that are spaced apart with respect to the center of the ring lamp by 360° divided by the number of viewing openings.

4. The system of claim 1 in which the number of viewing openings is two.

5. The system of claim 1 in which the number of viewing openings is three.

6. The system of claim 1 in which the number of viewing openings is four.

7. The system of claim 2 in which a ballast is used to regulate light output of the light source.

8. The system of claim 1 in which the chamber comprises two hemispheres that may be at least partially separated to replace the light source.

9. The system of claim 1 in which the chamber has a total surface area, and in which the chamber entrance and exit openings and viewing openings constitute a combined total opening area, and a ratio of the combined total opening area to the total surface area is less than 10%.

10. A shadowless illumination system, comprising:
a spherical chamber having a reflective inside surface, chamber entrance and exit openings, and at least two viewing openings;
a transparent tube positioned inside the chamber and extending from the chamber entrance opening to the chamber exit opening;
a light source providing illumination inside the chamber;
a first inspection camera having an optical axis that extends through a first one of the viewing openings toward a first point; and
a second inspection camera having an optical axis that extends through a second one of the viewing openings toward a second point;
whereby, the first and second cameras view articles passing through the tube and the chamber.

11. The system of claim 10 in which the first and second cameras view all portions of the articles passing through the tube.

12. The system of claim 10 in which the light source is a ring lamp positioned inside the chamber and around the tube.

13. The system of claim 12 in which the first and second points are on the ring lamp and spaced apart by 180°.

14. The system of claim 12 in which the first and second points are on the ring lamp and spaced apart by 90°.

15. The system of claim 10 in which there are only two cameras.

16. The system of claim 10 in which there is a third inspection camera having an optical axis that extends through a third one of the viewing openings toward a third point, and there are only three cameras.

17. The system of claim 10 in which there are third and fourth inspection cameras having respective optical axes that extend through respective third and fourth ones of the viewing openings toward respective third and fourth points, and there are only four cameras.

18. The system of claim 10 in which the chamber has a flat white inside surface with a reflectivity over 90%.

19. The system of claim 10 in which the tube is a cylinder.

20. The system of claim 10 in which the chamber has a total surface area, and in which the chamber entrance and exit openings and viewing openings constitute a combined total opening area, and a ratio of the combined total opening area to the total surface area is less than 10%.

* * * * *